United States Patent
Robin

(10) Patent No.: US 10,743,979 B2
(45) Date of Patent: *Aug. 18, 2020

(54) APPARATUS AND METHODS FOR REPAIRING ANEURYSMS

(71) Applicant: Endologix, Inc., Irvine, CA (US)

(72) Inventor: Marie Therese Robin, Tadworth (GB)

(73) Assignee: Endologix, Inc., Irvine, CA (US)

( * ) Notice: Subject to any disclaimer, the term of this patent is extended or adjusted under 35 U.S.C. 154(b) by 511 days.

This patent is subject to a terminal disclaimer.

(21) Appl. No.: 14/330,812

(22) Filed: Jul. 14, 2014

(65) Prior Publication Data

US 2015/0012081 A1 Jan. 8, 2015

Related U.S. Application Data

(63) Continuation of application No. 12/616,928, filed on Nov. 12, 2009, now Pat. No. 8,814,928, which is a continuation of application No. 10/481,386, filed as application No. PCT/GB02/02750 on Jun. 17, 2002, now Pat. No. 7,682,383.

(30) Foreign Application Priority Data

Jun. 19, 2001 (GB) .................................. 0114918.6

(51) Int. Cl.
  *A61F 2/07* (2013.01)
  *A61F 2/945* (2013.01)
  *A61F 2/89* (2013.01)

(52) U.S. Cl.
  CPC ................ *A61F 2/07* (2013.01); *A61F 2/945* (2013.01); *A61F 2/89* (2013.01); *A61F 2002/075* (2013.01); *A61F 2002/077* (2013.01); *A61F 2250/0003* (2013.01)

(58) Field of Classification Search
  CPC ................................................ A61F 2002/077
  See application file for complete search history.

(56) References Cited

U.S. PATENT DOCUMENTS

| | | |
|---|---|---|
| 5,122,154 A | 6/1992 | Rhodes |
| 5,330,528 A | 7/1994 | Lazim |
| 5,534,024 A | 7/1996 | Rogers et al. |
| 5,665,117 A | 9/1997 | Rhodes |
| 5,693,088 A | 12/1997 | Lazarus |
| 5,785,679 A | 7/1998 | Abolfathi et al. |
| 5,827,321 A | 10/1998 | Roubin et al. |

(Continued)

FOREIGN PATENT DOCUMENTS

| | | |
|---|---|---|
| WO | WO 91/07927 | 6/1991 |
| WO | WO 97/09008 | 3/1997 |

(Continued)

OTHER PUBLICATIONS

WO 01/21108 A1, Dehdashtian et al, Mar. 2001.*

(Continued)

*Primary Examiner* — Bruce E Snow
(74) *Attorney, Agent, or Firm* — Foley & Lardner LLP

(57) ABSTRACT

A device (100) for repairing an aneurysm by deployment within the aneurism comprises a graft tube, at least part thereof having an inflatable wall (102, 104) whereby the tube can be deployed in an artery and be inflated to grip at least part of the arterial wall.

19 Claims, 4 Drawing Sheets

(56) References Cited

U.S. PATENT DOCUMENTS

| | | | |
|---|---|---|---|
| 6,312,462 B1 | 11/2001 | McDermott et al. | |
| 6,312,463 B1 | 11/2001 | Rourke et al. | |
| 6,319,276 B1* | 11/2001 | Holman | A61B 17/12045 623/1.11 |
| 6,827,735 B2* | 12/2004 | Greenberg | A61B 17/12109 623/1.25 |
| 7,481,821 B2 | 1/2009 | Fogarty | |
| 7,530,988 B2 | 5/2009 | Evans et al. | |
| 7,682,383 B2 | 3/2010 | Robin | |
| 8,231,665 B2 | 7/2012 | Kim | |
| 8,231,666 B2 | 7/2012 | Kim | |
| 8,262,686 B2 | 9/2012 | Fogarty | |
| 8,535,367 B2 | 9/2013 | Kim | |
| 8,562,636 B2 | 10/2013 | Fogarty | |
| 8,562,662 B2 | 10/2013 | Kim et al. | |
| 8,647,377 B2 | 2/2014 | Kim | |
| 8,814,928 B2 | 8/2014 | Robin | |
| 8,936,633 B2 | 1/2015 | Kim et al. | |
| 9,005,235 B2 | 4/2015 | Fogarty et al. | |
| 2002/0026217 A1 | 2/2002 | Baker et al. | |
| 2003/0220666 A1 | 11/2003 | Mirigian et al. | |
| 2004/0210249 A1 | 10/2004 | Fogarty et al. | |
| 2006/0292206 A1 | 12/2006 | Kim et al. | |
| 2007/0050008 A1 | 3/2007 | Kim et al. | |
| 2007/0055355 A1 | 3/2007 | Kim et al. | |
| 2007/0061005 A1 | 3/2007 | Kim et al. | |
| 2009/0105748 A1 | 4/2009 | Fogarty et al. | |
| 2012/0303108 A1 | 11/2012 | Fogarty et al. | |
| 2012/0330343 A1 | 12/2012 | Kim et al. | |
| 2013/0261724 A1 | 10/2013 | Kim et al. | |
| 2014/0081374 A1 | 3/2014 | Kim et al. | |
| 2014/0088690 A1 | 3/2014 | Fogarty et al. | |

FOREIGN PATENT DOCUMENTS

| | | |
|---|---|---|
| WO | WO 97/19653 | 6/1997 |
| WO | WO-00/51522 | 9/2000 |
| WO | WO 01/21107 | 3/2001 |
| WO | WO 01/21108 | 3/2001 |
| WO | WO-01/66038 | 9/2001 |
| WO | WO-2004/043241 A2 | 5/2004 |
| WO | WO-2004/045393 A2 | 6/2004 |

OTHER PUBLICATIONS

European Search Opinion dated Mar. 20, 2013 for European Patent Application No. 10 011 024.6.
European Search Report dated Mar. 12, 2013 for European Patent Application No. 10 011 024.6.
Examination Report dated Jun. 9, 2015 for European Patent Application No. 10 011 024.6.
International Preliminary Examination Report dated Jun. 8, 2003 for PCT Application No. PCT/GB02/02750.
International Search Report dated Jul. 11, 2002 for PCT Application No. PCT/GB02/02750.
Notice of Allowance dated Apr. 23, 2014 for U.S. Appl. No. 12/616,928.
Notice of Allowance dated Jul. 24, 2009 for U.S. Appl. No. 10/481,386.
Response to First Written Opinion dated Jul. 2, 2003 for PCT/GB02/02750.
U.S. Office Action dated Aug. 20, 2007 for U.S. Appl. No. 10/481,386.
U.S. Office Action dated Jan. 17, 2014 for U.S. Appl. No. 12/616,928.
U.S. Office Action dated Jun. 13, 2013 for U.S. Appl. No. 12/616,928.
U.S. Office Action dated Jun. 8, 2012 for U.S. Appl. No. 12/616,928.
U.S. Office Action dated May 26, 2006 for U.S. Appl. No. 10/481,386.
U.S. Office Action dated Sep. 19, 2005 for U.S. Appl. No. 10/481,386.
Written Opinion dated Apr. 3, 2003 for PCT Application No. PCT/GB02/02750.
European Examination Report for EP Application No. 02 730 505.1, dated Oct. 14, 2015.
Piechota-Polanczyk, Aleksandra et al., "The abdominal aortic aneurysm and intraluminal thrombus: current concepts of development and treatment," Frontiers in Cardiovascular Medicine, vol. 2, Article 19, May 26, 2015.
Summons to attend oral proceedings dated Jul. 1, 2016, from EP application No. 02730505.1.

* cited by examiner

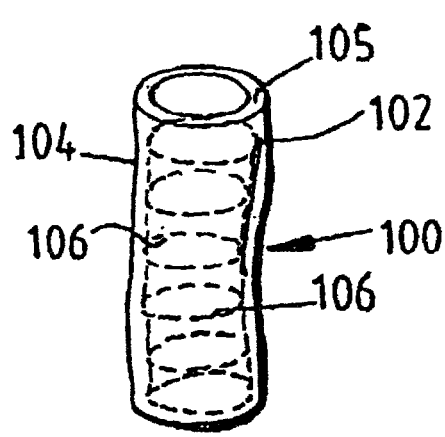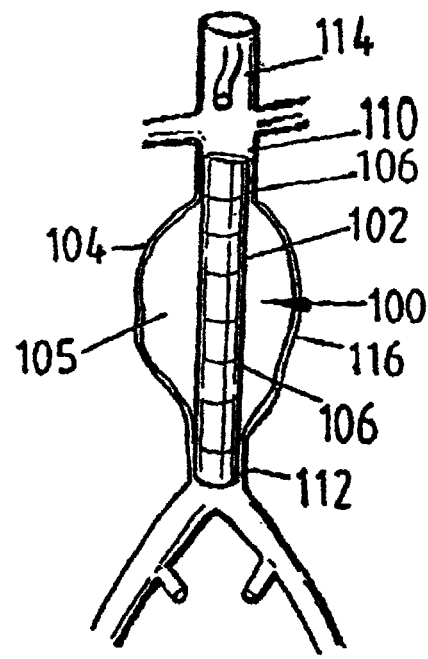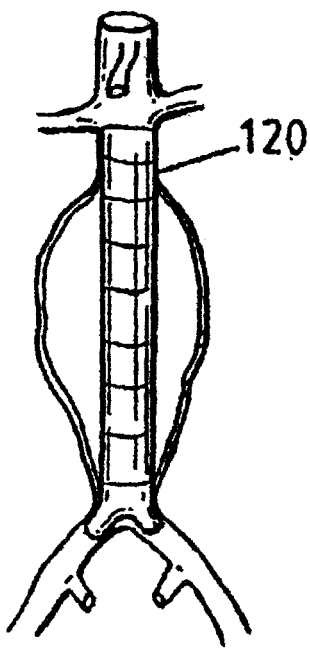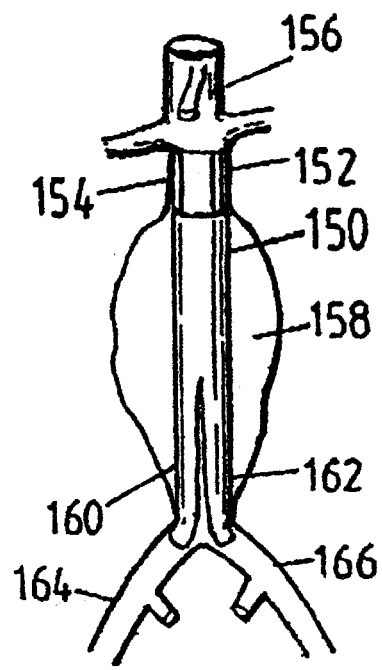

APPARATUS AND METHODS FOR REPAIRING ANEURYSMS

CROSS-REFERENCE TO RELATED PATENT APPLICATIONS

This application is a continuation of prior U.S. patent application Ser. No. 12/616,928 filed Nov. 12, 2009, which is a continuation of prior U.S. patent application Ser. No. 10/481,386 filed Dec. 19, 2003, which claims priority from International Application No. PCT/GB02/02750 filed Jun. 17, 2002 and from Great Britain patent application No. 0114918.6 filed Jun. 19, 2001, the entire disclosures of which are incorporated herein by reference.

DESCRIPTION

1. Field of the Invention

This invention concerns devices for use in repairing aneurysms, especially of the abdominal aorta.

2. Brief Discussion of the Related Art

An aneurysm occurs when an arterial wall becomes weakened to the extent that the weakened section balloons under pressure from the blood flowing through the artery. An aneurysm can lead to fatality if it ruptures causing rapid loss of blood.

An aortic aneurysm can be repaired by an endovascular repair procedure, in which a graft is inserted into the aneurysm via the femoral artery effectively to take the blood flow and to isolate the aneurysm. There are three forms of aortic endograft in current usage. The first is a straight stented tube graft. This may be used when there are adequate proximal and distal aortic necks for graft implantation. The tube may be stented at each end for support and to provide pins or hooks for embedding into the arterial wall to secure the tube in place. Alternatively, the tube may be stented throughout its length, such as by means of a metal wire stent. This form of endograft is used most commonly to repair aneurysms of the thoracic aorta.

An alternative construction of graft is a bifurcated tube for use in a patient with an abdominal aortic aneurysm where there is inadequate distal aortic neck but appropriate iliac artery configurations.

The third variation of endovascular graft is an aortouniliac graft, in which the tube extends from the proximal aortic neck into one of the iliac arteries. With this configuration an extraanatomic femofemoral bypass graft with a contralateral occlusion device in the common iliac artery is required. This device may be used when significant aneurismal disease is present in the contralateral iliac artery, precluding successful bifurcated graft placement.

A problem with such grafts is that over time, even over a period of two years, the graft can slip due to wear and tear on the stents, the effect of pulsatile blood flow through the tube and changes in the morphology of the arteries. The blood flow effect can be exaggerated as the graft slips and is able to bend and flex. Thus over time the integrity of the graft and isolation of the aneurysm can be compromised.

Another problem with stented grafts is that the twisting or flexing of the graft can cause fatigue in the metal stent. Such fatigue leads to fracturing of the stent wire and the resultant wire ends can pierce the graft material. Holes in the graft material mean that the aneurysm is no longer isolated from the blood flow.

Such grafts are generally used in a planned manner with the graft being selected for a specific patient according to precise pre-operative measurement of the aorta and adjacent arteries. Therefore, such grafts are not readily suited for use in repairing a ruptured aneurysm, where an emergency procedure is required simply to prevent death.

SUMMARY OF THE INVENTION

An object of this invention is to provide a device for use in repairing aneurysms that does not suffer from the above-mentioned disadvantages.

According to this invention there is provided a device for repairing an aneurysm by deployment within the aneurysm, the device comprising a graft tube, at least part thereof having an inflatable wall, whereby the tube can be deployed in an artery and be inflated to contact at least part of the arterial wall.

The term arterial wall may include arterial wall that is undamaged and/or aneurysm wall.

Graft tubes of the invention may be made of any suitable biologically compatible material and especially of plastics material.

Graft devices of the invention may be straight tubes or bifurcated tubes for use depending on the position and size of the aneurysm, i.e. for deployment in a similar manner to conventional endograft graft tubes. The graft tube of this embodiment may be one that narrows from one end to the other for use in aortouniliac grafting. The device of the invention may have an inflatable wall along its entire length or the device may have one or more discrete inflatable sections, especially at one or more ends of the tube.

Preferably the inflatable wall of the graft tube has an inner wall and an outer wall that is expandable in preference to the inner wall. The inner wall may be reinforced compared to the outer wall. Reinforcements of the inner wall may be, for example, by means of hoops, cages or mesh. Reinforcements may be of metal or plastics. Suitable metal reinforcement materials include stainless steel and nickel-titanium alloy. Suitable plastics reinforcement materials include inert polymers, such as, for example, polytetrafluoroethylene. Alternatively, the inner wall may be of a different material to the outer wall or may be of the same material but of different thickness to achieve the desired effect of the outer wall expanding upon inflation in preference to the inner wall with the inner wall substantially retaining its shape. The inflatable wall of the tube is preferably inflated by insertion of a settable material. Preferably the material is introduced as a liquid and sets to a solid or semi-solid state. The inflating material used will be biologically compatible and may, for example, be based on collagen or temperature/pH sensitive hydrogels, such as N-isopropyl acrylamide. It is possible that for stented graft tubes the inflating material need only set to a pliable condition. However, if the graft tube of the invention is to be deployed using a balloon to prevent an un-reinforced inner wall collapsing while the inflatable wall is being inflated, the inflating material may need to set to a relatively rigid condition.

The tube may be deployed in an aneurysm by inflating the tube, so that at least at the proximal artery position and ideally also at the distal artery position the tube grips the walls of the artery where there is no wall damage and between those positions the outer wall of the tube expands to contact the walls of the aneurysm and thereby support the aneurysm against flexing.

In one embodiment of the invention, a graft tube for use in repairing arterial aneurysms may have a first part with an inflatable wall to fit into the neck of the artery above an aneurysm. The remainder of the graft can be a straight, tapered or bifurcated tube.

Grafts of the invention may be deployed in an aortic aneurysm by means of conventional endovascular techniques. Typically, a guide wire is inserted through the femoral artery to extend beyond the aneurysm and the graft is guided into position along the wire. A narrow tube for inflating the twin walled part of the graft will be incorporated into the graft, one end of which will be accessible for the purpose of injection within the access wound in the groin. Once inflated to a desired extent the inflation tube is sealed.

Additionally or alternatively, a graft according to the invention may be deployed with the aid of an inflatable deployment balloon. Thus, a graft of the invention may be positioned in an aneurysm in collapsed form mounted on a deflated deployment balloon. The deployment balloon can then be inflated to seal the graft to the arterial wall above and below the aneurysm before the outer part of the graft is inflated by means of the settable material to conform to the anatomy of the aneurysm. Finally, the deployment balloon is deflated and withdrawn.

BRIEF DESCRIPTION OF THE DRAWINGS

This invention will now be further described, by way of example only, with reference to the accompanying drawings, in which:

FIG. 4 shows a first graft according to the invention;

FIG. 5 shows the graft of FIG. 4 in position in an aortic aneurysm;

FIG. 6 shows a second graft according to the invention in position in an aortic aneurysm;

FIG. 7 shows a third graft according to the invention in position in an aortic aneurysm;

DESCRIPTION OF THE PREFERRED EMBODIMENTS

Figure 1:
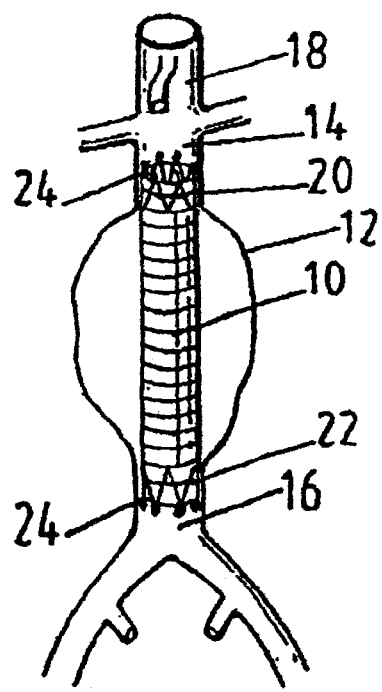
FIG. 1 shows a first prior art aortic aneurysm repair technique.

Referring to FIG. 1 of the accompanying drawings, a tubular graft 10 is shown deployed in an aortic aneurysm 12. The aneurysm is situated between proximal and distal regions 14, 16 respectively of the aorta 18. This deployment is possible when there is adequate aortic tissue above and below the aneurysm for attachment of the graft. The graft is stented (20, 22) at each end and has pins 24 extending from the stented regions for attachment to the aortic wall.

Figure 2:
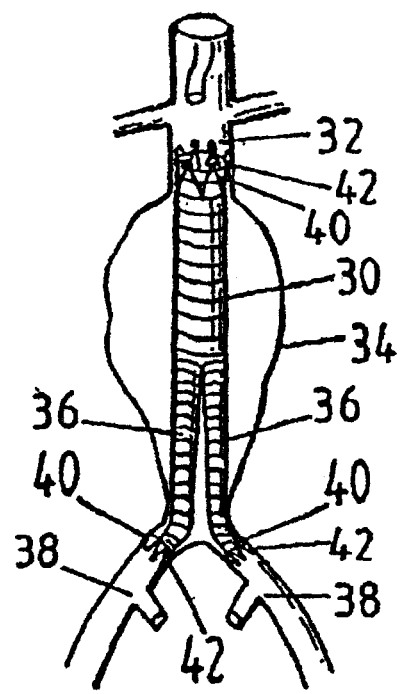
FIG. 2 shows a second prior art aortic aneurysm repair technique.

When there is inadequate aortic tissue below an aortic aneurysm for attachment of a graft as shown in FIG. 1 of the drawings, a bifurcated graft 30 can be used as shown in FIG. 2. Here the graft is attached in the neck 32 of the aorta above the aneurysm 34 and the two tube 36 resulting from the bifurcation are each deployed in an iliac artery 38 below the aneurysm. Again the ends of the graft are stented (40) and pins 42 are provided to aid attachment to the artery walls.

Figure 3:
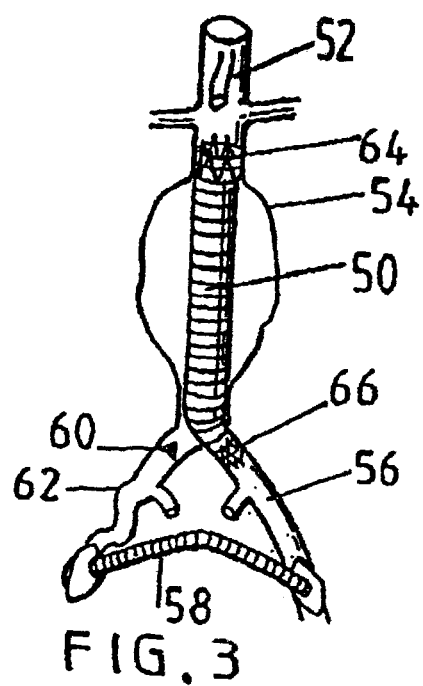
FIG. 3 shows a third prior art aortic aneurysm repair technique.
Figure 8:
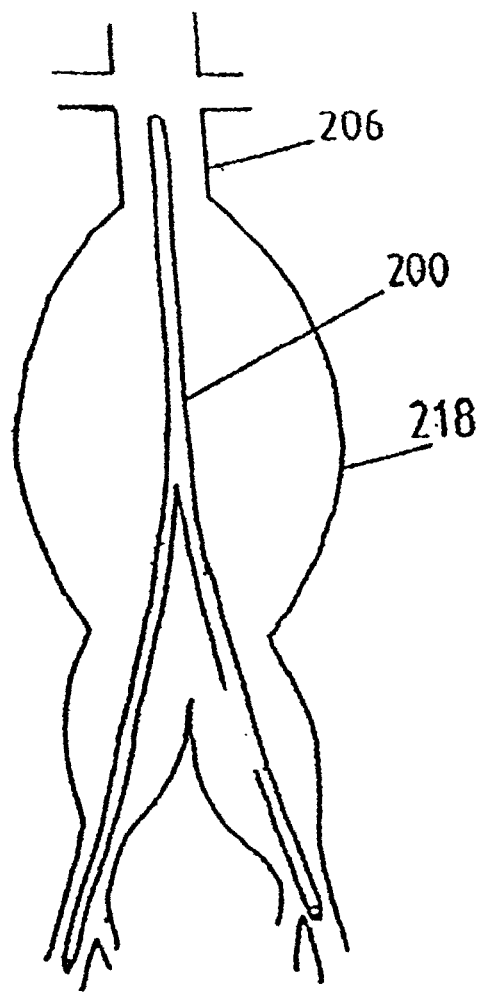
FIG. 8 shows a first stage of deployment of a fourth graft according to the invention.

If there is significant aneurismal disease in the contralateral iliac artery, which precludes use of a bifurcated graft of the type shown in FIG. 2, a graft 50 as shown in FIG. 3 may be used, which is deployed between the aorta 52 above the aneurysm 54 and the healthier iliac artery 56. The graft tube 50 narrows to compensate for the difference in widths of the aorta and iliac artery. With this procedure an extraanatomic femofemoral bypass 58 is required with a contralateral occlusion device 60 in the common iliac artery 62. Again this graft 50 is stented at both ends (64, 66).

Turning now to FIGS. 4 and 5 of the accompanying drawings, there is shown a tubular endovascular graft 100 of the invention for use in repairing an aortic aneurysm. The graft 100 is twin-walled having an inner wall 102 and an outer wall 104, whereby the space 105 between the walls can be inflated by introduction of inflating material.

The outer wall 104 is relatively expandable compared to the inner wall 102. Both walls may be of the same material but the inner wall reinforced, so that upon inflation, the outer wall expands to contact the aneurysm wall, as shown in FIG. 5, whilst the inner wall 102 retains substantially its diameter, so as not to affect adversely blood flow through the graft. The inner wall 102 as shown is reinforced with metal hoops 106, although the reinforcement can be of other materials or take a different form. An alternative may be to make the inner and outer walls of different materials to achieve a similar effect.

The graft 100 can be deployed in a similar manner to the graft shown in FIG. 1, i.e. between proximal and distal regions 110, 112 respectively of the aorta 114 above and below the aneurysm 116. When in position the graft is inflated by introduction of inflating material. This causes the outer wall of the graft to expand, firstly to grip the walls of the artery in those proximal and distal regions to fix the graft in place and secondly to contact the walls of the aneurysm to provide support therefor and, in the case of rupture, to seal the leakage of blood by direct closure of the tear in the aneurysm wall.

The inflating material is preferably a biocompatible material and may, for example, be based on collagen or temperature/pH sensitive hydrogels, such as N-isopropyl acrylamide. Preferably the inflating material is one that can be introduced as a liquid but which sets to from a pliable mass, such as in the nature of a gel. Once sufficient inflating material is introduced into the graft, possibly through a valve, the inflated graft is sealed.

In FIG. 6, a bifurcated graft 120 is shown which is similar in nature and general use to the graft 100 of FIGS. 4 and 5 but for the type of situation shown in FIG. 2 of the drawings, i.e. where there is aortic tissue damage requiring iliac artery deployment.

In FIG. 7 of the accompanying drawings there is shown an alternative form of inflatable tubular graft 150. The graft shown is a bifurcated graft but only a top portion 152 thereof is twin-walled. Thereby the graft 150 can be deployed and the top portion 152 inflated as with other embodiments of the invention to fix the graft in the proximal neck 154 of the aorta 156 above the aneurysm 158. The iliac tubes 160, 162 of the graft may be fixed in the iliac arteries 164, 166 in a conventional manner.

Turning to FIGS. 8 to 11 of the accompanying drawings, an endograft 200 comprises an inner graft tube 202 and an outer inflatable balloon 204 attached to the inner tube. The endograft shown is bifurcated but it could also be a single stem straight or tapered endograft. The outer balloon is designed to be inflated to conform to the anatomy of an aneurysm.

Figure 9:
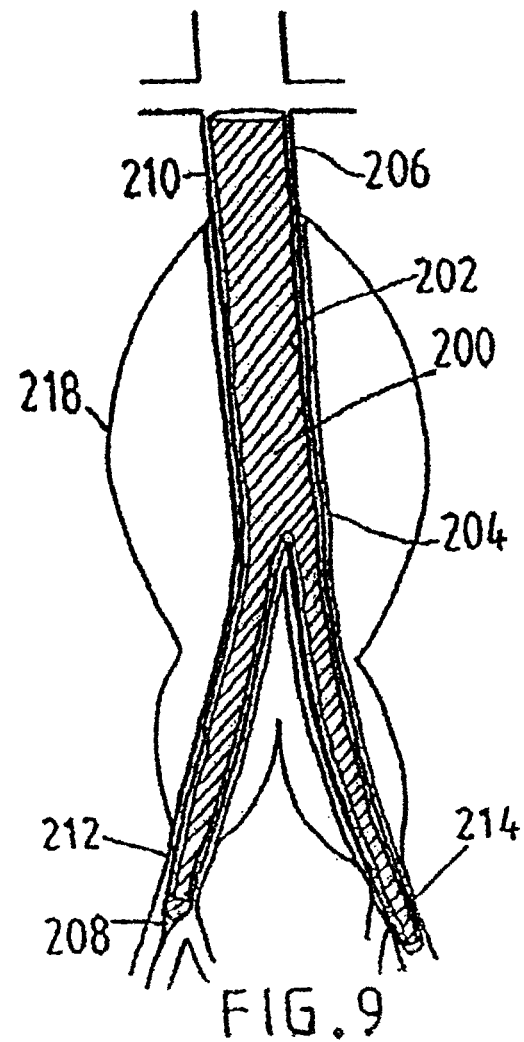
FIG. 9 shows a second stage in the deployment of the fourth graft according to the invention.
Figure 10:
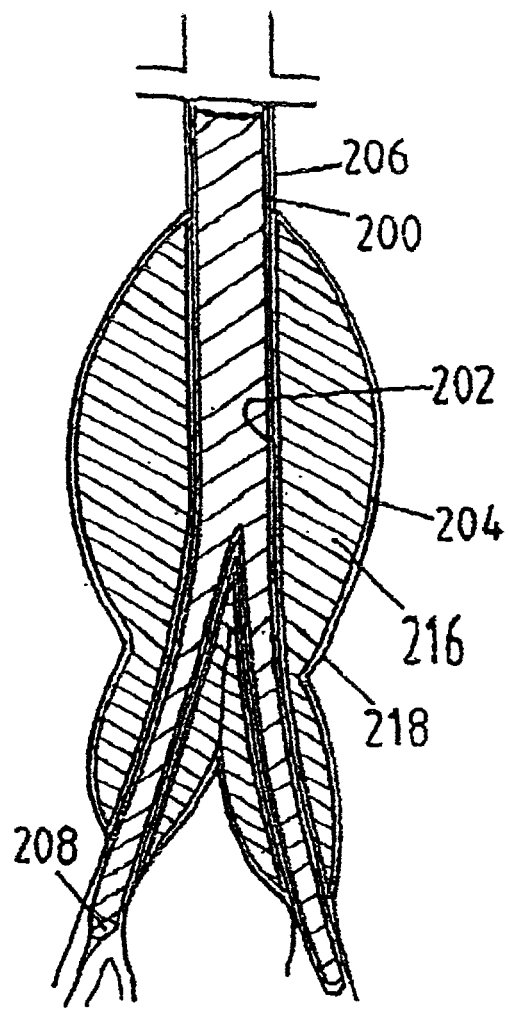
FIG. 10 shows a third stage in the deployment of the fourth graft according to the invention.
Figure 11:
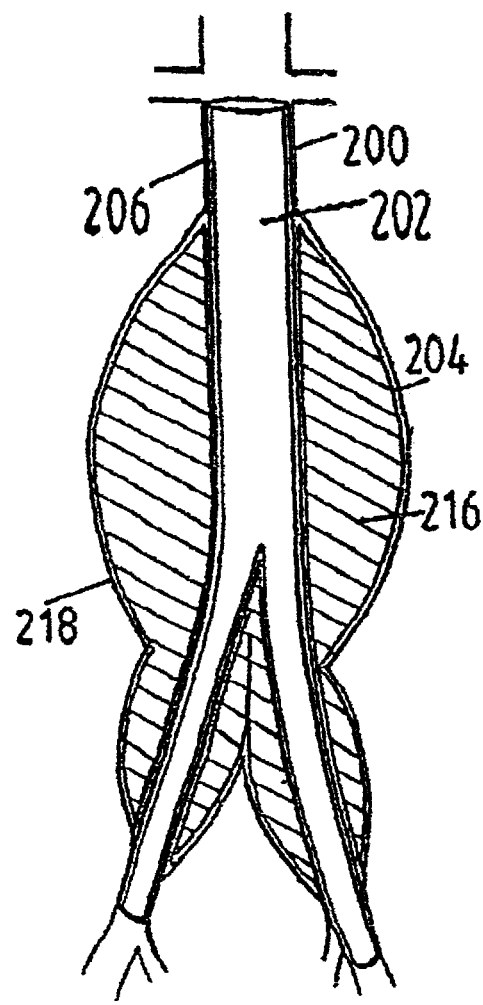
FIG. 11 shows a fourth stage in the deployment of the fourth graft according to the invention.

The endograft 200 is delivered into aorta 206 in a collapsed state mounted over an inflatable deployment balloon 208. Once the endograft is in position, the deployment balloon is inflated to expand the graft to form seals at the anastomoses 210, 212 and 214 of the aorta and iliac arteries (see FIG. 9). As seen in FIGS. 9 and 10, the deployment balloon 208, when inflated, supports the inner graft tube 202 along at least substantially the entire length of the inner graft tube 202. With the deployment balloon 208 still inflated, the outer balloon 204 of the endograft is inflated with a substance that rapidly sets to form a solid mass 216. Once that substance has set, the deployment balloon is deflated and removed, leaving the endograft supported by the inflated outer balloon that has conformed to the contours of the aneurysm sac 218.

Fixation of the endograft can then be enhanced by placement of stents (with or without barbs or hooks), which secure the upper and lower extremities of the graft to the surrounding arterial wall.

Advantages of grafts according to the invention include the possibility of rapid deployment, which, in the case of a ruptured aneurysm is vital, because the graft does not have to be designed for a particular patient. The ability to inflate the graft to fix it in place means that the same type of graft can be used in a variety of cases. The gel material used to inflate the device, by filling the aneurysm sac, will stabilize the endograft and prevent buckling, migration and leaking over time. The effects of post-operative changes in the morphology of the aneurysm sac and adjacent blood vessels will also be minimized with improved long-term stability of the repair.

Another possible advantage of graft devices of the invention is that they can be deployed without the need for stents, which means that the stent fatigue problem can be avoided.

The endografts of the invention are primarily intended for planned treatment of aneurysms but may also be used for emergency sealing of a ruptured aneurysm as a holding maneuver to stabilize a critically ill patient. Extensions and modifications may be made at a later date using additional inflatable or conventional endografts overlapping within the lumen of the first inflatable endograft using the "trombone" technique.

Inflated devices of the invention can seal aortic side branches and thereby completely isolate an aneurysm from systemic blood pressure.

The invention claimed is:

1. An apparatus, comprising:
an inner graft tube that bifurcates at a bifurcation point into a first branch of the inner graft tube and a second branch of the inner graft tube; and
an outer inflatable balloon attached to the inner graft tube;
the outer inflatable balloon extending from a first location above the bifurcation point to a second location below the bifurcation point and defining an inflatable space that is inflatable with a settable substance, the inflatable space of the outer inflatable balloon including a continuous volume below the bifurcation point from a bottom of the outer inflatable balloon on the first branch of the inner graft tube to a bottom of the outer inflatable balloon on the second branch of the inner graft tube.

2. The apparatus of claim 1, wherein the outer inflatable balloon extends across less than an entire length of the inner graft tube.

3. The apparatus of claim 1, further comprising an inflatable deployment balloon that when inflated supports the inner graft tube.

4. The apparatus of claim 1, wherein the outer inflatable balloon is positioned around the inner graft tube.

5. The apparatus of claim 1, wherein the outer inflatable balloon is formed of a different material than a material of the inner graft tube.

6. The apparatus of claim 1, wherein the apparatus further comprises the settable substance.

7. The apparatus of claim 1, wherein the apparatus further comprises the settable substance and the settable substance is introducable into the inflatable space as a liquid that rapidly sets to a solid or semi-solid state.

8. The apparatus of claim 1, wherein the apparatus further comprises the settable substance and the settable substance comprises collagen or a hydrogel.

9. The apparatus of claim 1, wherein the settable substance comprises N-isopropyl acrylamide.

10. The apparatus of claim 1, further comprising a stent for securing an upper extremity of the inner graft tube to an arterial wall.

11. An apparatus, comprising:
an inner graft tube that bifurcates at a bifurcation point into a first branch of the inner graft tube and a second branch of the inner graft tube, said inner graft tube having an unexpanded condition allowing deployment in an artery at the location of an aneurysm, said inner graft tube expandable within the artery from the unexpanded condition to an expanded condition; and
an outer inflatable balloon attached to the inner graft tube;
the outer inflatable balloon extending from a first location above the bifurcation point to a second location below the bifurcation point and defining an inflatable space that is inflatable with a settable substance, the inflatable space of the outer inflatable balloon including a continuous volume below the bifurcation point from a bottom of the outer inflatable balloon on the first branch of the inner graft tube to a bottom of the outer inflatable balloon on the second branch of the inner graft tube.

12. The apparatus of claim 11, further comprising a stent for securing an upper extremity of the inner graft tube to an arterial wall.

13. An apparatus, comprising:
an inner graft tube that bifurcates at a bifurcation point into a first branch of the inner graft tube and a second branch of the inner graft tube; and
an outer inflatable balloon that is expandable to conform to the contours of an aneurysm sac and that is attached to the inner graft tube;
the outer inflatable balloon extending from a first location above the bifurcation point to a second location below the bifurcation point and defining an inflatable space that is inflatable with a settable substance, the inflatable space of the outer inflatable balloon including a continuous volume below the bifurcation point from a bottom of the outer inflatable balloon on the first branch of the inner graft tube to a bottom of the outer inflatable balloon on the second branch of the inner graft tube.

14. The apparatus of claim 13, further comprising a deployment balloon that is configured to support the inner graft tube when the deployment balloon is inflated.

15. The apparatus of claim 13, wherein the apparatus includes the settable substance and the settable substance comprises collagen.

16. The apparatus of claim 13, wherein the apparatus includes the settable substance and the settable substance comprises a temperature sensitive hydrogel.

17. The apparatus of claim 13, wherein the apparatus includes the settable substance and the settable substance comprises a pH sensitive hydrogel.

18. The apparatus of claim 13, wherein the apparatus includes the settable substance and the settable substance comprises N-isopropyl acrylamide.

19. The apparatus of claim 13, further comprising a stent for securing an upper extremity of the inner graft tube to an arterial wall.

\* \* \* \* \*